United States Patent
Nguyen et al.

(10) Patent No.: US 9,044,416 B2
(45) Date of Patent: Jun. 2, 2015

(54) COSMETIC COMPOSITIONS CONTAINING PHENOLIC COMPOUNDS

(75) Inventors: Nghi Van Nguyen, Edison, NJ (US); Sawa Hashimoto, Garwood, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/702,993

(22) PCT Filed: Jun. 7, 2011

(86) PCT No.: PCT/US2011/039366
§ 371 (c)(1),
(2), (4) Date: Feb. 19, 2013

(87) PCT Pub. No.: WO2011/156311
PCT Pub. Date: Dec. 15, 2011

(65) Prior Publication Data
US 2013/0149264 A1    Jun. 13, 2013

Related U.S. Application Data

(60) Provisional application No. 61/352,153, filed on Jun. 7, 2010, provisional application No. 61/352,158, filed on Jun. 7, 2010, provisional application No. 61/352,146, filed on Jun. 7, 2010.

(51) Int. Cl.
| | | |
|---|---|---|
| *A61K 8/27* | (2006.01) | |
| *A61K 8/365* | (2006.01) | |
| *A61K 8/41* | (2006.01) | |
| *A61Q 5/00* | (2006.01) | |
| *A61K 8/97* | (2006.01) | |
| *A61K 8/84* | (2006.01) | |
| *A61Q 17/04* | (2006.01) | |
| *A61K 8/88* | (2006.01) | |

(52) U.S. Cl.
CPC ... *A61K 8/97* (2013.01); *A61K 8/27* (2013.01); *A61K 8/365* (2013.01); *A61K 8/84* (2013.01); *A61Q 5/00* (2013.01); *A61Q 17/04* (2013.01); *A61K 8/41* (2013.01); *A61K 8/88* (2013.01)

(58) Field of Classification Search
CPC .......... A61K 8/27; A61K 8/365; A61K 8/41; A61Q 17/04; A61Q 5/00
See application file for complete search history.

(56) References Cited

U.S. PATENT DOCUMENTS

| | | | |
|---|---|---|---|
| 2006/0182697 A1* | 8/2006 | Lalleman et al. | 424/59 |
| 2007/0110690 A1* | 5/2007 | Nguyen et al. | 424/70.1 |

FOREIGN PATENT DOCUMENTS

| | | | |
|---|---|---|---|
| EP | 1238654 B1 | * | 10/2008 |
| WO | WO 8706833 A1 | * | 11/1987 |

OTHER PUBLICATIONS

Ou, S.; Kwok, K-C. "Ferulic acid: pharmaceutical functions, preparation and applications in foods" J. Sci. Food Agric. 2004, 84, 1261-1269.*
Zinc Oxide Properties (http://www.zinc.org/info/zinc_oxide_properties), 2011; accessed Jan. 12, 2015.*

* cited by examiner

*Primary Examiner* — Sean Basquill
*Assistant Examiner* — Andrew S Rosenthal
(74) *Attorney, Agent, or Firm* — John A. Artz; Dickinson Wright PLLC

(57) ABSTRACT

A method of photoprotecting a keratinous substrate comprising applying a composition onto the keratinous substrate, the composition comprising at least one phenolic compound chosen environmental at least one ortho-diphenol, at least one phenolic compound having a carboxylic acid moiety, and mixtures thereof, —a compound chosen from at least one pelyarn!ne, at least one water solvable metal salt, and mixtures thereof; and a cosmetically acceptable carrier. The present disclosure also relates to photoprotective compositions for application onto hair and skin, the compositions comprising at least one phenolic compound chosen from at least one ortho-diphenol, at least one phenolic compound having a carboxylic acid moiety, and mixtures thereof; a compound chosen from at least one polyamine, at least one water soluble metal salt, and mixtures thereof; and a cosmetically acceptable carrier.

18 Claims, No Drawings

COSMETIC COMPOSITIONS CONTAINING PHENOLIC COMPOUNDS

CROSS-REFERENCE TO RELATED APPLICATIONS

This application claims the benefit of the filing date of U.S. Provisional Patent Application Nos. 61/352,146, 61/352,153 and 61/352,158, filed Jun. 7, 2010, the disclosures of which are hereby incorporated herein by reference.

TECHNICAL FIELD

The present invention relates to methods and compositions of photoprotecting keratinous substrates using phenolic compounds and a compound chosen from at least one polyamine, at least one water soluble metal salt, or mixtures thereof.

BACKGROUND OF THE DISCLOSURE

It is known that UV and visible radiations can damage keratinous substrates such as skin and hair and as a result, there are rising concerns among consumers and experts alike regarding the effects of these radiations on the human body. Cosmetic and personal care products aimed at protecting keratinous substrates, in particular the skin, from visible and ultraviolet light, are readily available, with particular emphasis on applying sunscreen to the skin before sun exposure. However, sun exposure of unprotected hair can also have deleterious effects on the hair, resulting in, for example, the degradation of the natural and artificial color of hair, dry and brittle hair, reduced strength of the hair fibers and an overall unhealthy appearance to the hair which is undesirable to the consumer.

Photoprotective or sunscreen compositions currently available to consumers tend to easily be removed from the body upon contact with water. This can occur upon bathing in the ocean or in a swimming pool, in the shower or when engaged in water sports. Conventional photoprotective or sunscreen compositions do not continue to provide the desired photoprotection as soon as the keratinous substrate to which they have been applied comes in contact with water, thereby leaving the consumer unsatisfied with the efficacy of available photoprotective products. Thus, there is still a need to improve currently marketed anti-sun or sunscreen compositions which impart to the keratinous substrates effective photoprotection. There also continues to be a need for such compositions to be stable over time and resistant to water and that provide other desirable benefits such as more conditioned hair, less damaged hair and a better look and feel to the hair.

Thus one of the objects of this invention is related to a composition and method that will provide desirable photoprotective benefits to keratinous substrates such as hair and minimize the deleterious effect of the sun on hair.

It has been surprisingly and unexpectedly discovered that a composition containing the combination of a phenolic compound and a second compound chosen from at least one polyamine, at least one water soluble metal salt, or mixtures thereof imparts highly desirable cosmetic benefits such as less damaged hair, durability on the hair, shine on hair, improvements in the retention and enhancement of artificial or natural hair color, and hair fiber strength.

Moreover, the use of this composition on keratinous substrates, such as hair and skin, can result in desirable and beneficial effects, such as improved conditioning and protection from environmental and chemical damage.

BRIEF SUMMARY OF THE DISCLOSURE

The present invention is directed to a method of photoprotecting a keratinous substrate comprising applying a composition onto the keratinous substrate, the composition comprising:
(a) at least one phenolic compound chosen from at least one ortho-diphenol, at least one phenolic compound having a carboxylic acid moiety, and mixtures thereof;
(b) a compound chosen from at least one polyamine, at least one water soluble metal salt, and mixtures thereof;
(c) a cosmetically acceptable carrier.

The present invention is also directed to a photoprotective composition for application onto hair and skin, the composition comprising at least one phenolic compound chosen from at least one ortho-diphenol, at least one phenolic compound having a carboxylic acid moiety, and mixtures thereof; a compound chosen from at least one polyamine, at least one water soluble metal salt, and mixtures thereof; and a cosmetically acceptable carrier.

DETAILED DESCRIPTION OF THE DISCLOSURE

Other than in the operating examples, or where otherwise indicated, all numbers expressing quantities of ingredients and/or reaction conditions are to be understood as being modified in all instances by the term "about," meaning within 10% to 15% of the indicated number.

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

"At least one" as used herein means one or more and thus includes individual components as well as mixtures/combinations.

The term "water-soluble metal salt" as used herein is understood to mean any organic or inorganic metal salt having a solubility of more than 0.2 grams at 25 degrees Celsius per liter of water.

The compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to keratinous materials.

The present invention relates to a method for treating a keratinous substrate such as hair, the method involving the steps of providing a hair cosmetic composition containing at least one phenolic compound chosen from at least one ortho-diphenol, at least one phenolic compound having a carboxylic acid moiety, or mixtures thereof; A second compound chosen from at least one polyamine, at least one water soluble metal salt, or mixtures thereof; and a cosmetically acceptable carrier, and applying said composition onto the keratinous substrate.

The present invention also relates to compositions for application onto hair and which may be utilized in leave-on conditioners, permanent waving compositions, hair coloring products, hair care products, hair treatment and hair masque products, and hair styling products. The compositions of the present invention may also be utilized in other personal care compositions such as body washes, skin care, sun care, nail care and facial care. In addition, such compositions may be used in makeup products such as foundation, eye color, lip color and lip gloss.

It is to be understood that both the foregoing general description and the following detailed description are exemplary and explanatory only, and are not restrictive of the invention.

Phenolic Compound

The at least one phenolic compound of the present invention can be chosen from ortho-diphenols, phenolic compounds having a carboxylic acid moieties, and mixtures thereof.

Ortho-Diphenol

The at least one ortho-diphenol compound of the present invention can be chosen from phenolic compounds, polyphenolic compounds, catechol compounds, catechin/epicatechin compounds, betacyanin compounds, polycyclic compounds having at least one 1,2-dihydroxybenzene moiety, and mixtures thereof.

The at least one ortho-diphenol compound of the present invention can also contain one or more substitutents on the aromatic ring wherein said one or more substituents are ortho-diphenolic groups.

The at least one ortho-diphenol compound of the present invention can also contain one or more substitutents on the aromatic ring wherein said one or more substituents have one or more ortho-diphenolic groups.

The at least one ortho-diphenol compound of the present invention may be chosen from compounds of Formula I:

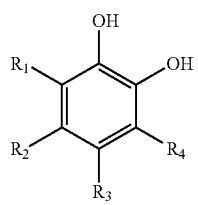

(I)

wherein the $R_1$, $R_2$, $R_3$, and $R_4$ substituents, which are identical or different, represent a hydrogen atom, an —OH group, a heteroatom, an amine, a substituted amine, —NO$_2$, a methyl, a saturated or unsaturated, substituted or unsubstituted, linear or branched alkyl radical, a saturated or unsaturated, substituted or unsubstituted, linear or branched alkenyl radical, substituted or unsubstituted, a substituted or unsubstituted heterocyclic radical, cycloalkyl radical, a substituted or unsubstituted aryl group, alkylaryl group wherein the alkyl is saturated or unsaturated, substituted or unsubstituted, linear or branched, an alkoxy group, an alkoxyalkyl group, an alkoxyaryl group, a carboxylate group, a radical containing one or more silicon atoms, —COOH, —OCOR$_5$, —COOR$_5$, —R$_6$—COOH, —R$_6$—COOR$_5$, —CH=CH—R$_5$, —CH=CH—COOR$_5$, —CO—R$_5$, —CHOH—R$_5$, —OOC—R$_5$, —CHR$_5$—CH$_3$, where two of the components $R_1$ to $R_4$ jointly form a saturated or unsaturated cycle optionally containing one or more heteroatoms and optionally condensed with one or more saturated or unsaturated cycles optionally containing one or more heteroatoms, and wherein group $R_5$ is chosen from a hydrogen atom, an —OH group, a heteroatom, an amine, a substituted amine, —NO$_2$, a methyl, a saturated or unsubstituted, linear or branched alkyl radical, a saturated or unsaturated, substituted or unsubstituted, linear or branched alkenyl radical, substituted or unsubstituted, a substituted or unsubstituted heterocyclic radical, cycloalkyl radical, a substituted or unsubstituted aryl group, alkylaryl group wherein the alkyl is saturated or unsaturated, substituted or unsubstituted, linear or branched, an alkoxy group, an alkoxyalkyl group, an alkoxyaryl group, a carboxylate group, a radical containing one or more silicon atoms, and a carboxylate group and wherein $R_6$ is chosen from an alkyl radical, alkenyl radical, aryl radical, alkylaryl radical, and alkenylaryl radical.

In addition, the $R_1$, $R_2$, $R_3$, and $R_4$ substituents of the at least one ortho-diphenol compound according to Formula (I) can independently be ortho-diphenolic groups and/or can contain one or more ortho-diphenolic groups.

The at least one ortho-diphenol compound of the present invention may also be chosen from polycyclic compounds having at least one 1,2-dihydroxybenzene moiety wherein the at least one 1,2-dihydroxybenzene moiety can be substituted with a group chosen from a hydrogen atom, an —OH group, a heteroatom, an amine, a substituted amine, —NO$_2$, a methyl, a saturated or unsaturated, substituted or unsubstituted, linear or branched alkyl group, alkylaryl group wherein the alkyl is saturated or unsaturated, substituted or unsubstituted, linear or branched, a carboxylate group, —COOH, —OCOR, —COOR, —R—COOH, —R—COOR, —CH=CH—R, —CH=CH—COOR, —CO—R, —CHOH—R, —OOC—R, —CHR—CH3, and wherein group R is independently chosen from a hydrogen atom, an —OH group, a heteroatom, a methyl, a saturated or unsaturated, substituted or unsubstituted, linear or branched alkyl group, a substituted or unsubstituted cyclic group, a substituted or unsubstituted heterocyclic group, a substituted or unsubstituted aryl group, an alkylaryl group wherein the alkyl is saturated or unsaturated, substituted or unsubstituted, linear or branched, a carboxylate group, an amine, a substituted amine, and —NO$_2$.

The at least one ortho-diphenol compound of the present invention may be chosen from flavonols, anthocyanidins, anthocynanins, hydroxybenzoates, flavones, and iridoids which may be osylated or glucosylated and/or may be in the form of oligomers (procyanidins).

Examples of the at least one ortho-diphenol compound of the present invention are caffeoylquinic acid, caffeic acid, dihydrocaffeic acid, n-hexadecyl caffeate, caffeoyltartaric acid, chlorogenic acid, rosmarinic acid, oleuropein, hydroxytyrosol, pyrogallol, quercetin, myricetin, luteolin, isoquercitrin, carnosic acid, rutin, baicalein, gallic acid, epigallocatechol gallate, ethylhexyl gallate, digalloyl trioleate, catechin, epicatechin, epigallocatechol gallate epigallocatechin, cichoric acid, and mixtures thereof.

The at least one ortho-diphenol compound of the present invention includes ortho-diphenol compounds derived from plant extracts, fruit extracts, citrus fruit extracts, and vegetable extracts.

The at least one ortho-diphenol compound may also be present in the compositions of the present disclosure as components of plant extracts, fruit extracts, citrus fruit extracts, and vegetable extracts, the extracts themselves being added to said compositions.

The plant extracts include rose and tea extracts.

The fruit extracts include apple, grape (more particularly, grape seeds), blueberry, pomegranate, and banana extracts.

The vegetable extracts include potato extracts.

It is also possible to use plant and/or fruit extract blends such as apple and tea extract blends and grape and apple extract blends.

The at least one ortho-diphenol compound of the present invention includes phenolic compounds, polyphenolic compounds, catechol compounds, catechin/epicatechin compounds, betacyanin compounds, and polycyclic compounds having at least one 1,2-dihydroxybenzene moiety which have antioxidant properties.

The at least one ortho-diphenol compound of the present invention is preferably chosen from dihydroxycinnamates, such as caffeic acid, its salts and esters and mixtures thereof.

Phenolic Compound Having at Least One Carboxylic Acid Moiety

The at least one phenolic compound having at least one carboxylic acid moiety of the present invention may be chosen from compounds of Formula I:

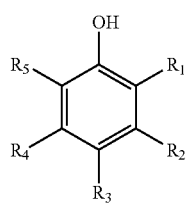

(I)

wherein the $R_1$, $R_2$, $R_3$, $R_4$ and $R_5$ substituents, which are identical or different, represent a hydrogen atom, an —OH group, a heteroatom, an amine, a substituted amine, —$NO_2$, a methyl, a saturated or unsaturated, substituted or unsubstituted, linear or branched alkyl radical, a saturated or unsaturated, substituted or unsubstituted, linear or branched alkenyl radical, substituted or unsubstituted, a substituted or unsubstituted heterocyclic radical, cycloalkyl radical, a substituted or unsubstituted aryl group, alkylaryl group wherein the alkyl is saturated or unsaturated, substituted or unsubstituted, linear or branched, an alkoxy group, an alkoxyalkyl group, an alkoxyaryl group, a carboxylate group, a radical containing one or more silicon atoms, —COOH, —$OCOR_6$, —$COOR_6$, —$R_7$—COOH, —$R_7$—$COOR_6$, —CH=CH—$R_6$, —CH=CH—$COOR_6$, —CO—$R_6$, —CHOH—$R_6$, —OOC—$R_6$, —$CHR_6$—CH3, where two of the components $R_1$ to $R_5$ jointly form a saturated or unsaturated cycle optionally containing one or more heteroatoms and optionally condensed with one or more saturated or unsaturated cycles optionally containing one or more heteroatoms, wherein group $R_6$ is chosen from a hydrogen atom, an —OH group, a heteroatom, an amine, a substituted amine, —$NO_2$, a methyl, a saturated or unsaturated, substituted or unsubstituted, linear or branched alkyl radical, a saturated or unsaturated, substituted or unsubstituted, linear or branched alkenyl radical, substituted or unsubstituted, a substituted or unsubstituted heterocyclic radical, cycloalkyl radical, a substituted or unsubstituted aryl group, alkylaryl group wherein the alkyl is saturated or unsaturated, substituted or unsubstituted, linear or branched, an alkoxy group, an alkoxyalkyl group, an alkoxyaryl group, a carboxylate group, a radical containing one or more silicon atoms, and a carboxylate group, wherein $R_7$ is chosen from an alkyl radical, alkenyl radical, aryl radical, alkylaryl radical, and alkenylaryl radical and wherein at least one of the $R_1$ to $R_5$ substituents is a carboxylic acid moiety (—COOH) and/or at least one of the $R_1$ to $R_5$ substituents carries a carboxylic acid moiety (—COOH).

The at least one phenolic compound having at least one carboxylic acid moiety of the present invention may also be chosen from polycyclic compounds.

The at least one phenolic compound having at least one carboxylic acid moiety of the present invention can also contain one or more substitutents on the aromatic ring wherein said one or more substitutents are phenolic groups which may be substituted with carboxylic acid moieties.

The at least one phenolic compound having at least one carboxylic acid moiety of the present invention can also contain one or more substitutents on the aromatic ring wherein said one or more substitutents have phenolic groups which may be substituted with carboxylic acid moieties.

The at least one phenolic compound having at least one carboxylic acid moiety of the present invention may be chosen from flavonols, anthocyanidins, anthocynanins, hydroxybenzoates, flavones, and iridoids which may be osylated or glucosylated and/or may be in the form of oligomers (procyanidins).

Examples of the at least one phenolic compound having at least one carboxylic acid moiety of the present invention are ferulic acid, caffeoylquinic acid, caffeic acid, dihydrocaffeic acid, n-hexadecyl caffeate, caffeoyltartaric acid and its derivatives, chlorogenic acid, rosmarinic acid, oleuropein, hydroxytyrosol, pyrogallol, quercetin, myricetin, luteolin, isoquercitrin, carnosic acid, rutin, baicalein, kaempferol, gallic acid, epigallocatechol gallate, ethylhexyl gallate, digalloyl trioleate, digalloyl trioleate, catechin, epicatechin, epicatechin-3-gallate, epigallocatechin, epigallocatechin-3-gallate, peonidin, oenin, cichoric acid, coumaric acid, quinic acid, and mixtures thereof.

The at least one phenolic compound having at least one carboxylic acid moiety of the present invention includes ortho-diphenol compounds derived from plant extracts, fruit extracts, citrus fruit extracts, and vegetable extracts.

The at least one phenolic compound having at least one carboxylic acid moiety may also be present in the compositions of the present disclosure as components of plant extracts, fruit extracts, citrus fruit extracts, and vegetable extracts, the extracts themselves being added to said compositions.

The plant extracts include rose and tea extracts.

The fruit extracts include apple, grape (more particularly, grape seeds), blueberry, pomegranate, and banana extracts.

The vegetable extracts include potato extracts.

It is also possible to use plant and/or fruit extract blends such as apple and tea extract blends and grape and apple extract blends.

The at least one phenolic compound having at least one carboxylic acid moiety of the present invention includes polyphenolic compounds, catechol compounds, catechin/epicatechin compounds, betacyanin compounds, and polycyclic compounds which have antioxidant properties.

A phenolic compound having at least one carboxylic acid moiety suitable for use in the present invention is ferulic acid.

Another phenolic compound having at least one carboxylic acid moiety suitable for use in the present invention is caffeic acid.

Particularly preferred phenolic compounds of the present invention are green tea extract, also known as *Camellia Sinensis* Leaf Extract, ferulic acid, and caffeic acid.

The at least one phenolic compound of the present invention is present in an amount ranging from greater than 0% by weight to about 20% by weight, preferably from about 0.05% to about 10% by weight, more preferably from about 0.1% to about 5% by weight, by weight, based on the total weight of the composition of the present invention.

Polyamine

The at least one polyamine compound of the present invention comprises at least two amino groups and typically comprises at least 3 amino groups.

The at least one polyamine may, for example, be chosen from a polyethyleneimine, a polyvinylamine, an aminated polysaccharide, an amine substituted polyalkylene glycol, an amine substituted polyacrylate crosspolymer, an amine substituted polyacrylate, an amine substituted polymethacrylate, an aminosilicone, a protein, an amine substituted polyester, a polyamino acid, an amodimethicone, a polyalkylamine, diethylene triamine, triethylenetetramine, spermidine, spermine and mixtures thereof.

The at least one polyamine may also, for example, be chosen from alkoxylated polyamines.

The at least one polyamine compound may, for example, be chosen from polymers such as homopolymers comprising at least three amino groups, copolymers comprising at least three amino groups, and terpolymers comprising at least three amino groups. Thus, the at least one polyamine compound comprising at least three amino groups may be chosen from, for example, polymers comprising at least three amino groups formed from (i) at least one monomer unit comprising at least one amino group as defined herein, and, optionally, (ii) at least one additional monomer unit different from the at least one monomer (i); and polymers comprising at least three amino groups formed from (i) at least one monomer comprising at least three amino groups as defined herein, and, optionally, (ii) at least one additional monomer unit different from the at least one monomer (i). According to the present invention, the at least one additional monomer different from the at least one monomer (i) may or may not comprise at least one amino group as defined herein.

The at least one polyamine may also be chosen from polyethyleneimines (also commonly designated as PEI). Polyethyleneimines suitable for use in the compositions of the present invention may optionally be substituted. Non-limiting examples of polyethyleneimine include Lupasol® products commercially available from BASF. Suitable examples of Lupasol® polyethyleneimines include Lupasol® PS, Lupasol® PL, Lupasol® PR8515, Lupasol® G20, Lupasol® G35 as well as Lupasol® SC Polyethyleneimine Reaction Products (such as Lupasol® SC-61B, Lupasol® SC-62J, and Lupasol® SC-86X). Other non-limiting examples of polyethyleneimines which may be used in the composition according to the present invention are the Epomin® products commercially available from Aceto. Suitable examples of Epomin® polyethyleneimines include Epomin® SP-006, Epomin®SP-012, Epomin® SP-018, and Epomin® P-1000. These examples include substituted polyethyleneimines.

Polyamines suitable for use in the present invention may also be chosen from polyvinylamines. Examples thereof include Lupamines® 9095, 9030, 9010, 5095, 1595 from BASF.

The at least one polyamine compound may, for example, be chosen from aminated polysaccharides comprising at least three amino groups.

Polyamines suitable for use in the present invention include an aminosilicone includes Dow Corning® 2-8566 Amino Fluid, an amino functional polydimethylsiloxane fluid from Dow Corning®.

Another suitable polyamine is an amine substituted polyacrylate crosspolymer, including Carbopol Aqua CC polymer from Noveon, Inc.

The at least one polyamine compound may also be chosen from proteins and protein derivatives. Non-limiting examples of suitable proteins and protein derivatives for use in the present invention include those listed at pages 2719 to 2722 of the C.T.F.A. International Cosmetic Ingredient Dictionary and Handbook, 11th edition, vol. 3, (2006).

In one embodiment, the at least one polyamine compound is chosen from wheat protein, soy protein, oat protein, collagen, and keratin protein.

The at least one polyamine compound may also be chosen from compounds comprising lysine, compounds comprising arginine, compounds comprising histidine, and compounds comprising hydroxylysine.

In one embodiment, the at least one polyamine compound includes polylysine, chitosan, polyarginine, and mixtures thereof.

Non-limiting preferred examples of suitable alkoxylated polyamines include hydrocarbyl amines which have at least one primary nitrogen atom and include compounds corresponding to formula (I):

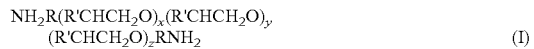

$$NH_2R(R'CHCH_2O)_x(R'CHCH_2O)_y(R'CHCH_2O)_zRNH_2 \quad (I)$$

wherein R represents a —$CHCH_3$— or —$C(CH_3)_2$— group, or a hydrocarbon radical containing at least 3 carbon atoms that can be linear or branched, acyclic or cyclic, saturated or unsaturated, aliphatic or aromatic, substituted or unsubstituted;

x, y, and z independently of one another, represent numbers of from 0 to 100;

R' represents hydrogen, or an alkyl group, preferably a methyl group; and the sum of x+y+z is at least 1.

In formula (I), R is preferably a linear or branched, acyclic alkyl or alkenyl group or an alkyl phenyl group; x, y, and z independently of one another, preferably represent numbers ranging from 2 to 100.

Examples of the alkoxylated polyamines for use in the present invention which correspond to formula (I) include, for example, tetradecyloxypropyl-1,3-diaminopropane; $C_{12-14}$ alkyl oxypropyl-1,3-diaminopropane; $C_{12-15}$ alkyloxypropyl amine and other similar materials that are commercially available from Tomah under the tradename of TOMAH® DA-17.

Other examples of alkoxylated polyamines of Formula (IA) are diamine compounds belonging to the Jeffamine series such as the Jeffamine® D and Jeffamine® ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. Jeffamine® D series compounds are amine terminated PPGs (polypropylene glycols) and Jeffamine® ED series compounds are polyether diamine based with a predominantly PEG (polyethylene glycol) backbone.

Other non-limiting preferred examples of suitable alkoxylated polyamines in the diamine form include compounds corresponding to formula (II):

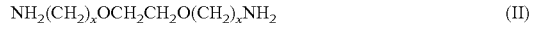

$$NH_2(CH_2)_xOCH_2CH_2O(CH_2)_xNH_2 \quad (II)$$

wherein x is 2 or 3.

Examples of alkoxylated polyamines of Formula (II) are diamine compounds belonging to the JEFFAMINE series available from Huntsman Corporation, Salt Lake City, Utah, such as JEFFAMINE EDR148, and JEFFAMINE EDR176.

Additional non-limiting preferred examples of alkoxylated polyamines in the triamine form include compounds corresponding to formula (III):

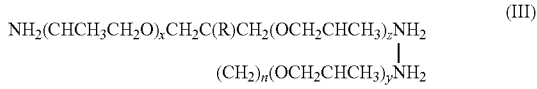

wherein R is hydrogen or —$C_2H_5$,
n=0 or 1, and
x, y, and z independently of one another, represent numbers of from 0 to 100 and the sum of x+y+z is at least 1.

Examples of alkoxylated polyamines for use in the present invention which correspond to formula (III) are triamine compounds belonging to the Jeffamine series such as the Jeffamine® T series available from Huntsman Corporation, Salt Lake City, Utah. Examples of the Jeffamine® T series compounds are JEFFAMINE T403, JEFFAMINE T3000, and JEFFAMINE T5000. Jeffamine® T series compounds are triamines made by reacting PO with a triol initiator followed by aminating the terminal hydroxyl groups.

Another type of preferred alkoxylated polyamines include compounds of formulas (IV) and (V) hereunder:

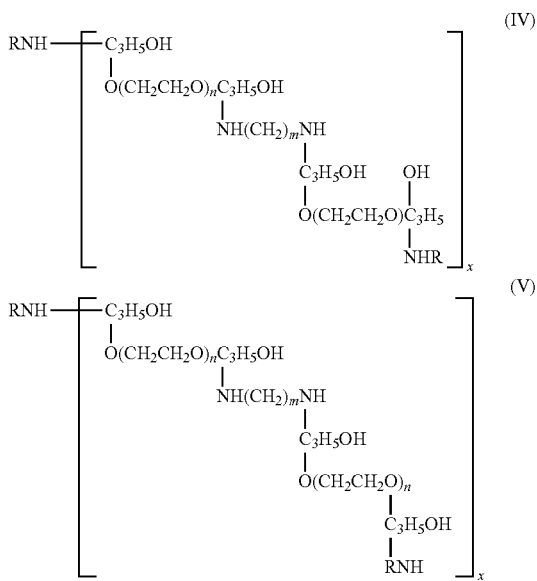

wherein
R in formula (IV) represents the alkyl group derived from tallow and R in formula (V) represents the alkyl group derived from coconut oil;
n in both formulas (IV) and (V) has a total value ranging from 10 to 20;
m in both formulas (IV) and (V) has a value ranging from 2 to 6; and
x in both formulas (IV) and (V) has a value ranging from 2 to 4.

Examples of alkoxylated polyamines of Formulas (IV) and (V) are PEG-15 Tallow Polyamine and PEG-15 Coco-polyamine, respectively.

Particularly preferred polyamines of the present invention include LUPASOL® G 35, polyethyleneimine, commercially available from BASF; and Jeffamine ED-400, polyethylene glycol diamine, commercially available from Huntsman Corporation.

The at least one polyamine is present in the composition of the present invention in an amount ranging from greater than 0% by weight to about 50% by weight, preferably from about 0.05 to about 40% by weight, more preferably from about 0.1 to about 30% by weight, even more preferably from about 0.1 to about 20% by weight, based on the total weight of the composition.

Water-Soluble Metal Salt

The at least one water-soluble metal salt of the present invention may be selected from a large number of compounds, wherein the metal donor may be selected from Ti, V, Cr, Mn, Fe, Co, Ni, Cu, Zn, Se, Sr, Be, Ba, Ca, Mg, Al and Mo.

The at least one water-soluble metal salt of the present invention may be chosen from polyvalent metal salts, including divalent metal salts.

The at least one water-soluble metal salt of the present invention may be also chosen from chloride, bromide, fluoride, iodide, sulfate, nitrate, phosphate, citrate, acetate salts, carboxylic acid salts and mixtures thereof.

The at least one water-soluble metal salt of the present invention is preferably a divalent metal salt.

Examples of the at least one water-soluble metal salt are zinc chloride, magnesium chloride, ferrous chloride, manganese chloride, cupric chloride, calcium chloride, cobalt dichloride, zinc sulfate, magnesium sulfate, ferrous sulfate, manganese sulfate, copper sulfate, cobalt sulfate, zinc acetate, magnesium acetate, ferrous acetate, manganese acetate, cupric acetate, calcium acetate, cobalt acetate, magnesium citrate, ferrous citrate, manganese citrate, calcium chloride, calcium citrate and mixtures thereof.

The at least one water-soluble metal salt of the present invention is preferably a divalent metal chloride salt such as zinc chloride, calcium chloride, and mixtures thereof.

The at least one water-soluble metal salt of the present invention is present in an amount ranging from greater than 0% by weight to about 20% by weight, preferably from about 0.05% to about 10% by weight, more preferably from about 0.1% to about 5% by weight, based on the total weight of the composition of the present invention.

Cosmetically Acceptable Carrier

The at least one cosmetically acceptable carrier may be chosen from water, organic solvents and mixtures thereof. By way of organic solvent, suitable examples may be chosen from C1-C4 lower alkanols, such as ethanol and isopropanol; for example, polyols and polyol ethers such as 2-butoxyethanol, propylene glycol, propylene glycol monomethyl ether, diethylene glycol monoethyl ether and monomethyl ether, for example, and aromatic alcohols such as benzyl alcohol or phenoxyethanol, for example, and mixtures thereof. Other examples of solvents for use in the present invention are hexyleneglycol and dipropylene glycol, and mixtures thereof.

In one embodiment of the present invention, the cosmetically acceptable carrier is water.

In another embodiment of the present invention, the cosmetically acceptable carrier is an organic solvent.

In another embodiment of the present invention, the cosmetically acceptable carrier is a polar organic solvent.

In one preferred embodiment of the present invention, the cosmetically acceptable carrier comprises water, at least one organic solvent and mixtures thereof.

In another preferred embodiment of the present invention, the cosmetically acceptable carrier comprises a solvent chosen from water, at least one alcohol and mixtures thereof.

The at least one cosmetically acceptable carrier is present in an amount ranging from about 1% to about 99.9% by weight, preferably from about 2% to about 95% by weight, more preferably from about 5% to about 80% by weight, based on the total weight of the composition of the present invention.

Other cosmetically acceptable carriers may include mineral oils, silicone oils, synthetic or natural esters, fatty acids, humectants, straight chain hydrocarbons, isoparaffins, esters, silicone oils, waxes and mixtures thereof. The cosmetically acceptable carriers may also include polybutene, hydrogenated polyisobutene, hydrogenated polydecene, polydecene, squalene, petrolatum, and mixtures thereof. Amounts of these materials may range from about 0.1 to about 95%, preferably from about 0.5 to about 50%, more preferably from about 1 to about 20% by weight of the composition.

The composition(s) of the present invention may also comprise organic and inorganic sunscreens or UV filters.

The composition(s) of the present invention may also comprise additives, for instance those chosen from the non-exhaustive list such as rheology-modifying agents, film-forming agents, conditioning agents, humectants, reducing agents, surfactants, antioxidants, sequestering agents, softeners, antifoams, moisturizers, emollients, basifying agents, gelling agents, wetting agents, thickening agents, spreading agents, dispersants, plasticizers, preservatives, sunscreens, direct dyes or oxidation dyes, pigments, mineral fillers, clays, colloidal minerals, nacres, nacreous agents, emulsifying agents, fragrances, peptizers, preserving agents, fixing or non-fixing polymers, ceramides, proteins, active agents, vitamins, anti-dandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The compositions of the present invention can be formulated as oil-in-water or water-in-oil emulsions, water-silicone emulsions, aqueous compositions, and aqueous-alcoholic compositions.

The compositions of the present invention can also be in the form of sprays, mousses, creams, lotions, paste, and gels.

According to one embodiment of the present invention, there is provided a method for photoprotecting keratinous substrates, such as hair, by applying the above-disclosed composition onto the keratinous material.

According to another embodiment of the present invention, there is provided a method for photoprotecting keratinous substrates, such as skin, by applying the above-disclosed composition onto skin.

According to one preferred embodiment of the present invention, there is provided a composition for photoprotecting keratinous substrates, such as hair and skin, the composition containing at least one phenolic compound and at least one water soluble metal salt, wherein the at least one phenolic compound and the at least one water soluble metal salt are present in the composition in amounts effective to protect the keratinous substrates from UV damage.

According to another preferred embodiment of the present invention, there is provided a composition for photoprotecting keratinous substrates, such as hair and skin, the composition containing at least one phenolic compound and at least one polyamine, wherein the at least one phenolic compound and the at least one polyamine are present in the composition in effective amounts such that the composition has an enhanced photoprotective property.

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, unless otherwise specified.

EXAMPLE 1

Hair Treatment Composition Containing Caffeic Acid and Zinc Chloride

Hair fibers taken from natural white hair were prepared and soaked for 20 minutes in solutions A, B, and C and in a 60:40 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Caffeic acid | 1.0% | 1.0% | | |
| Zinc chloride | 0.76% | | 0.76% | |
| Water/ethanol (60:40) | 98.24% | 99.00% | 99.24% | 100% |

After soaking, the hair fibers from each treatment were divided into two sets—one set of hair fibers was dried and exposed to UV radiation (Xenotest, 45 W/m2, 40 hours, 70% relative humidity (RH), 35° C. and the other set of hair fibers was not exposed to UV radiation.

The exposed and unexposed hair was analyzed by HP-DSC (Differential Scanning calorimetry), at 80-180° C. at 10° C./minute, in order to determine $T_d$, the denaturation temperature for each hair fiber sample. The % efficiency in hair protection against UV radiation was calculated using the formula:

$$\frac{[(T_d\ \text{Control})_{Unexp} - (T_d\ \text{Control})_{Exp}] - [(T_d\ \text{Test})_{Unexp} - (T_d\ \text{Test})_{Exp}]}{[(T_d\ \text{Control})_{Unexp} - (T_d\ \text{Control})_{Exp}]} \times 100$$

A higher calculated % efficiency means greater protection against UV damage.

The results obtained were:

| Solution | % efficiency |
|---|---|
| A | 42.72% |
| B | 22.5% |
| C | −13.01% |

The data above shows that the hair treated with the solution (A) containing Zn salt and an ortho-diphenol compound performed significantly better than the hair treated with the solution containing the ortho-diphenol compound alone or the Zn salt alone.

EXAMPLE 2

Hair Treatment Composition Containing Green Tea Extract and Zinc Chloride

Hair fibers taken from natural white hair were prepared and soaked for 20 minutes in solutions A, B, and C and in a 60:40 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Green Tea Extract | 1.0% | 1.0% | | |
| Zinc chloride | 0.76% | | 0.76% | |
| Water/ethanol (60:40) | 98.24% | 99.00% | 99.24% | 100% |

After soaking, the hair fibers were exposed to UV radiation (Xenotest) and analyzed by HP-DSC following the procedure above in Example 1.

The results obtained were:

| Solution | % efficiency |
|---|---|
| A | 47.24% |
| B | 19.43% |
| C | −13.01% |

The data above shows that the hair treated with the solution (A) containing Zn salt and green tea extract performed significantly better than the hair treated with the solution containing the green tea extract alone or the Zn salt alone.

EXAMPLE 3

Hair Treatment Composition Containing Ferulic Acid and Polyethyleneimine

Hair fibers taken from natural white hair were prepared and soaked for 20 minutes in solutions A, B, and C and in a 70:30 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Ferulic acid | 1.0% | 1.0% | | |
| Polyethyleneimine | 0.27% | | 0.27% | |
| Water/ethanol | 98.73% | 99.00% | 99.73% | 100% |

After soaking, the hair fibers from each treatment were divided into two sets—one set of hair fibers was dried and exposed to UV radiation (Xenotest, 45 W/m2, 40 hours, 70% relative humidity (RH), 35° C. and the other set of hair fibers was not exposed to UV radiation.

The exposed and unexposed hair was analyzed by HP-DSC (Differential Scanning Calorimetry), at 80-180° C. at 10° C./minute, in order to determine $T_d$, the denaturation temperature for each hair fiber sample. The % efficiency in hair protection against UV radiation was calculated using the formula:

$$\frac{[(T_d \text{ Control})_{Unexp} - (T_d \text{ Control})_{Exp}] - [(T_d \text{ Test})_{Unexp} - (T_d \text{ Test})_{Exp}]}{[(T_d \text{ Control})_{Unexp} - (T_d \text{ Control})_{Exp}]} \times 100$$

A higher calculated % efficiency means greater protection against UV damage,

The results obtained were:

| Solution | % efficiency |
|---|---|
| A | 44.79% |
| B | 16.18% |
| C | 27.33% |

The data above shows that the hair treated with the solution (A) containing polyethyleneimine and ferulic acid was better protected against UV damages than hair treated with ferulic acid alone or with polyethyleneimine alone.

EXAMPLE 4

Hair Treatment Composition Containing Ferulic Acid and Polylysine

Hair fibers taken from natural white hair were prepared and soaked for 20 minutes in solutions A, B, and C and in a 70:30 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Ferulic Acid | 1.0% | 1.0% | | |
| Polylysine | 0.28% | | 0.28% | |
| Water/ethanol | 98.72% | 99.00% | 99.72% | 100% |

After soaking, the hair fibers were exposed to UV radiation (Xenotest) and analyzed by HP-DSC following the procedure above in Example 3.

The results obtained were:

| Solution | % efficiency |
|---|---|
| A | 34.52% |
| B | 16.18% |
| C | 13.14% |

The data above shows that the hair treated with the solution (A) containing polylysine and ferulic acid was better protected against UV damages than hair treated with ferulic acid alone or with polylysine alone.

EXAMPLE 5

Hair Treatment Composition Containing Ferulic Acid and Polypropylene Glycol Diamine (PolyPPGDiamine, Jeffamine D4000)

Hair fibers taken from natural white hair were prepared and soaked for 20 minutes in solutions A, B, and C and in a 60:40 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Ferulic Acid | 1.0% | 1.0% | | |
| PolyPPGDiamine | 1.65% | | 1.65% | |
| Water/ethanol | 97.35% | 99.00% | 99.46% | 100% |

After soaking, the hair fibers were exposed to UV radiation (Xenotest) and analyzed by HP-DSC following the procedure above in Example 3.

The results obtained were:

| Solution | % efficiency |
|---|---|
| A | 33.15% |
| B | 16.18% |
| C | −1.06% |

The data above shows that the hair treated with the solution (A) containing PolyPPGDiamine and ferulic acid was better protected against UV damages than hair treated with ferulic acid alone or with PolyPPGDiamine alone.

EXAMPLE 6

Hair Treatment Composition Containing Ferulic Acid and Polyethylene Glycol Diamine (PolyPEGDiamine, Jeffamine ED400)

Hair fibers taken from natural white hair were prepared and soaked for 20 minutes in solutions A, B, and C and in a 60:40 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Ferulic Acid | 2.5% | 2.5% | | |
| PolyPEGDiamine | 11.25% | | 11.25% | |
| Water/ethanol | 86.25% | 97.5% | 88.75% | 100% |

After soaking, the hair fibers were exposed to UV radiation (Xenotest) and analyzed by HP-DSC following the procedure above in Example 3.

The results obtained were:

| Solution | % efficiency |
|---|---|
| A | 52.78% |
| B | 21.15% |
| C | 0.35% |

The data above shows that the hair treated with the solution (A) containing PolyPEGDiamine and ferulic acid was better protected against UV damages than hair treated with ferulic acid alone or with PolyPEGDiamine alone.

EXAMPLE 7

Hair Treatment Composition Containing Ferulic Acid, Polyethyleneimine and Zinc Chloride Hair fibers taken from natural white hair were prepared and soaked for 20 minutes in solutions A, B, and C and in a 60:40 water/ethanol mixture (D, control) (each solution adjusted to pH 7.0 with HCl or NaOH):

| Ingredient | % by weight in A (Test) | % by weight in B (Test) | % by weight in C (Test) | % by weight in D (Control) |
|---|---|---|---|---|
| Caffeic acid | 1.0% | 1.0% | 1.0% | |
| Polyethyleneimine | 0.59% | | | |
| Zinc Chloride | 0.76% | 0.76% | | |
| Water/ethanol | 97.65% | 98.24% | 99.0% | 100% |

After soaking, the hair fibers from each treatment were divided into two sets—one set of hair fibers was dried and exposed to UV radiation (Xenotest, 45 W/m2, 40 hours, 70% relative humidity (RH), 35° C. and the other set of hair fibers was not exposed to UV radiation.

The exposed and unexposed hair was analyzed by HP-DSC (Differential Scanning calorimetry), at 80-180° C. at 10° C./minute, in order to determine $T_d$, the denaturation temperature for each hair fiber sample. The % efficiency in hair protection against UV radiation was calculated using the formula:

$$\frac{[(T_d \text{ Control})_{Unexp} - (T_d \text{ Control})_{Exp}] - [(T_d \text{ Test})_{Unexp} - (T_d \text{ Test})_{Exp}]}{[(T_d \text{ Control})_{Unexp} - (T_d \text{ Control})_{Exp}]} \times 100$$

A higher calculated % efficiency means greater protection against UV damage.

The results obtained were:

| Solution | % efficiency |
|---|---|
| A | 66.86% |
| B | 42.72% |
| C | 22.50% |

The data above shows that the hair treated with the solution (A) containing polyethyleneimine, caffeic acid and zinc chloride was better protected against UV damages than hair treated with the caffeic acid-Zinc chloride combination alone or with caffeic acid alone.

What is claimed is:

1. A method of photoprotecting hair comprising applying a composition onto the hair, the composition comprising:
   (a) at least one phenolic compound chosen from at least one ortho-diphenol, at least one phenolic compound having a carboxylic acid moiety, and mixtures thereof;
   (b) at least one polyamine;
   (c) at least one water soluble zinc metal salt that does not comprise zinc oxide; and
   (d) a cosmetically acceptable carrier;
   wherein hair is photoprotected.

2. The method according to claim 1, wherein (a) is chosen from compounds derived from plant extracts, fruit extracts, citrus fruit extracts, and vegetable extracts.

3. The method according to claim 1, wherein (a) is an ortho-diphenol compound chosen from phenolic compounds, polyphenolic compounds, catechol compounds, catechin/epicatechin compounds, betacyanin compounds, polycyclic compounds having at least one 1,2-dihydroxybenzene moiety, and mixtures thereof.

4. The method according to claim 1, wherein (a) is an ortho-diphenol compound chosen from caffeoylquinic acid, caffeic acid, dihydrocaffeic acid, n-hexadecyl caffeate, caffeoyltartaric acid, chlorogenic acid, rosmarinic acid, oleuropein, hydroxytyrosol, pyrogallol, quercetin, myricetin, luteolin, isoquercitrin, carnosic acid, rutin, baicalein, gallic acid, epigallocatechol gallate, ethylhexyl gallate, digalloyl trioleate, catechin, epicatechin, epigallocatechol gallate epigallocatechin, cichoric acid, and mixtures thereof.

5. The method according to claim 1, wherein (a) is a phenolic compound having a carboxylic acid moiety chosen from polyphenolic compounds, catechol compounds, catechin/epicatechin compounds, betacyanin compounds, polycyclic compounds, and mixtures thereof.

6. The method according to claim 1, wherein (a) is a phenolic compound having a carboxylic acid moiety chosen from ferulic acid, caffeoylquinic acid, caffeic acid, dihydrocaffeic acid, n-hexadecyl caffeate, caffeoyltartaric acid and its derivatives, chlorogenic acid, rosmarinic acid, oleuropein, hydroxytyrosol, pyrogallol, quercetin, myricetin, luteolin, isoquercitrin, carnosic acid, rutin, baicalein, kaempferol, gallic acid, epigallocatechol gallate, ethylhexyl gallate, digalloyl trioleate, digalloyl trioleate, catechin, epicatechin, epicatechin-3-gallate, epigallocatechin, epigallocatechin-3-gallate, peonidin, oenin, cichoric acid, coumaric acid, quinic acid, and mixtures thereof.

7. The method according to claim 1, wherein (a) is selected from ferulic acid and caffeic acid, their salts, their esters and mixtures thereof.

8. The method according to claim 1, wherein (a) is present in an amount ranging from greater than 0% by weight to about 20% by weight, based on the total weight of the composition.

9. The method according to claim 1, wherein (a) is present in an amount ranging from greater than 0.1% by weight to about 5% by weight, based on the total weight of the composition.

10. The method according to claim 1, wherein (b) is a polyamine chosen from a polyethyleneimine, a polyvinylamine, an aminated polysaccharide, an amine substituted polyalkylene glycol, an amine substituted polyacrylate crosspolymer, an amine substituted polyacrylate, an amine substituted polymethacrylate, an aminosilicone, a protein, an amine substituted polyester, a polyamino acid, an amodimethicone, a polyalkylamine, diethylene triamine, triethylenetetramine, spermidine, spermine and mixtures thereof.

11. The method according to claim 1, wherein (b) the polyamine is selected from polyethyleneimine, an alkoxylated polyamine, and a polyamino acid chosen from polylysine, polyarginine, chitosan, and mixtures thereof.

12. The method according to claim 1, wherein (b) the polyamine is present in an amount ranging from greater than 0% by weight to about 50% by weight, based on the total weight of the composition.

13. The method according to claim 1, wherein (b) the polyamine is present in an amount ranging from about 0.1 to about 20% by weight, based on the total weight of the composition.

14. The method according to claim 1, wherein (b) is a water soluble metal salt chosen from a water soluble divalent metal salt.

15. The method according to claim 1, wherein (b) is zinc chloride.

16. The method according to claim 1, wherein (b) is a water soluble metal salt present in an amount ranging from greater than 0% by weight to about 20% by weight, based on the total weight of the composition.

17. The method according to claim 1, wherein (b) is a water soluble metal salt present in an amount ranging from about 0.1% to about 5% by weight, based on the total weight of the composition.

18. The method according to claim 1, wherein (d) is chosen from water, alcohol, organic solvents, hydrocarbons, esters, silicones, and mixtures thereof.

* * * * *